United States Patent
Dierre et al.

(10) Patent No.: US 9,400,335 B2
(45) Date of Patent: Jul. 26, 2016

(54) X-RAY RADIATION DETECTOR AND CT SYSTEM

(71) Applicant: Siemens Aktiengesellschaft, Munich (DE)

(72) Inventors: Fabrice Dierre, Granville (FR); Björn Kreisler, Hausen (DE); Miguel Labayen De Inza, Forchheim (DE); Daniel Niederlöhner, Erlangen (DE); Christian Schröter, Bamberg (DE); Matthias Strassburg, Klagenfurt (AT)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 0 days.

(21) Appl. No.: 14/418,096

(22) PCT Filed: Jul. 10, 2013

(86) PCT No.: PCT/EP2013/064535
§ 371 (c)(1),
(2) Date: Jan. 29, 2015

(87) PCT Pub. No.: WO2014/019822
PCT Pub. Date: Feb. 6, 2014

(65) Prior Publication Data
US 2015/0260856 A1 Sep. 17, 2015

(30) Foreign Application Priority Data
Jul. 31, 2012 (DE) .................. 10 2012 213 410

(51) Int. Cl.
*G01T 1/24* (2006.01)
*H01L 31/0224* (2006.01)
(Continued)

(52) U.S. Cl.
CPC ............... *G01T 1/241* (2013.01); *A61B 6/4208* (2013.01); *H01L 31/0224* (2013.01); *H01L 31/115* (2013.01); *A61B 6/032* (2013.01); *A61B 6/4014* (2013.01)

(58) Field of Classification Search
CPC ............................. G01T 1/24; A61B 6/4208
See application file for complete search history.

(56) References Cited

U.S. PATENT DOCUMENTS

| 6,163,030 A | 12/2000 | Johnson et al. |
| 7,652,258 B2 | 1/2010 | Shahar et al. |

(Continued)

FOREIGN PATENT DOCUMENTS

| CN | 1817306 A | 8/2006 |
| JP | H0983007 A | 3/1997 |

(Continued)

OTHER PUBLICATIONS

International Search Report PCT/ISA/210 for International Application No. PCT/EP2013/064535 dated Jan. 10, 2014.
(Continued)

*Primary Examiner* — David Porta
*Assistant Examiner* — Faye Boosalis
(74) *Attorney, Agent, or Firm* — Harness, Dickey & Pierce, P.L.C.

(57) ABSTRACT

A direct-converting x-ray radiation detector is disclosed for detecting x-ray radiation, at least including a semiconductor used to detect x-ray radiation and at least one electrode attached to the semiconductor. In an embodiment, the semiconductor and the at least one electrode are electrically conductively connected and the at least one electrode is designed to be transparent and electrically conductive. A CT system is further disclosed, at least including the direct-converting x-ray radiation detector.

30 Claims, 3 Drawing Sheets

(51) Int. Cl.
*H01L 31/115* (2006.01)
*A61B 6/03* (2006.01)
*A61B 6/00* (2006.01)

(56) References Cited

U.S. PATENT DOCUMENTS

| | | | |
|---|---|---|---|
| 8,624,105 B2* | 1/2014 | Routkevitch | C01B 3/042 |
| | | | 136/244 |
| 2004/0195515 A1 | 10/2004 | Wheeler et al. | |
| 2008/0164418 A1 | 7/2008 | Shahar et al. | |
| 2008/0224180 A1 | 9/2008 | Nariyuki | |
| 2008/0237770 A1 | 10/2008 | Iwazaki | |
| 2010/0086098 A1 | 4/2010 | Shahar et al. | |
| 2010/0304204 A1 | 12/2010 | Routkevitch et al. | |
| 2011/0253886 A1 | 10/2011 | Hackenschmied et al. | |
| 2012/0068078 A1 | 3/2012 | Zhang et al. | |

FOREIGN PATENT DOCUMENTS

| | | |
|---|---|---|
| JP | 2008227346 A | 9/2008 |
| JP | 2008251999 A | 10/2008 |
| JP | 2009118943 A1 | 6/2009 |
| WO | WO-02103389 A2 | 12/2002 |
| WO | WO-2014/019817 A2 | 2/2014 |

OTHER PUBLICATIONS

Written Opinion of the International Searching Authority PCT/ISA/237 for International Application No. PCT/EP2013/064535 dated Jan. 10, 2014.
Korean Office Action and English translation thereof dated Nov. 29, 2015.
Chinese Office Action issued in Chinese Patent Application No. 2013800485025, dated Jan. 11, 2016.
Korean Office Action mailed Apr. 8, 2016.

\* cited by examiner

X-RAY RADIATION DETECTOR AND CT SYSTEM

PRIORITY STATEMENT

This application is the national phase under 35 U.S.C. §371 of PCT International Application No. PCT/EP2013/064535 which has an International filing date of Jul. 10, 2013, which designated the United States of America, and which claims priority to German patent application DE 102012213410.7 filed Jul. 31, 2012, the entire contents of each of which are hereby incorporated herein by reference.

FIELD

At least one embodiment of the invention generally relates to a direct-converting X-ray radiation detector for detecting X-ray radiation, in particular for use in a CT system, at least including a semiconductor used to detect X-ray radiation, and at least one electrode attached to the semiconductor, wherein the semiconductor and the at least one electrode are electrically conductively connected; and at least one embodiment generally relates to a CT system including an X-ray radiation detector.

BACKGROUND

Among others, direct-converting detectors based on semiconducting materials, such as CdTe, CdZnTe, CdZnTeSe, CdTeSe, CdMnTe, InP, TlBr2, HgI2, are used for the detection of gamma and X-ray radiation, in particular in CT, dual-energy CT, SPECT and PET systems. However, these materials have a large number of crystal defects or impurities which may be electrically active as capture and recombination centers and have an adverse effect on the detection of X-ray radiation, by way of example in the form of image artifacts.

In order to optimize X-ray radiation detection it is known to irradiate the semiconductor used for detection with an additional radiation to produce additional charge carriers. Infrared, ultraviolet or visible radiation by way of example is used as additional radiation. In the previously known X-ray radiation detectors, however, non-transparent or opaque electrodes have been used which are arranged on the side face of the semiconductor facing the additional radiation. This non-transparent electrode also connects the material of the semiconductor to a high voltage source or an electrically conductive connection to the high voltage source. The applied high voltage generates an electric field inside the material of the semiconductor which enables movement of the generated charge carriers with respect to the electrode. However, in a non-transparent electrode, the semiconductor is almost completely shielded from the additional radiation, so no additional charge carriers are generated.

Conventional electrodes also exhibit a significant absorption effect for the X-ray radiation to be detected. Due to the requirement to keep the dose rate of a patient in a CT scanner as low as possible, it is desirable to use an electrode with the lowest possible absorption effect. This applies regardless of whether the detector is irradiated with additional radiation or not in order to optimize the X-ray radiation detection.

A direct-converting X-ray radiation detector is known from printed publication U.S. Pat. No. 7,652,258 B2, in which the polarization effects are to be reduced with the aid of additionally irradiated IR radiation in a transparent intermediate layer.

Reference is also made to printed publication US 2012/0068078 A1 which discloses a radiation detector having a semiconductor made from HgJ2, with electrodes made from palladium, TiW, ITO, SnO2, InO3 or carbon membranes, on which a protection layer of silicone or parylene is formed.

Printed publication U.S. Pat. No. 6,163,030 A also discloses a radiation detector having a semiconductor in which electrodes made from TCO, thin metal layers of Au or Pt, or organic conductors such as polyaniline are used.

Finally, reference is also made to printed publication US 2011/0253886 A1 which describes a direct-converting radiation detector, in which light is coupled into a semiconductor layer with the aid of a light source.

SUMMARY

In at least one embodiment of the invention, an improved direct-converting X-ray radiation detector is disclosed whose detector material is not shielded by a non-transparent electrode from additional radiation and whose electrode has a low absorption effect for the gamma and/or X-ray radiation to be detected.

Advantageous developments of the invention are the subject matter of subordinate claims.

The inventors have recognized that it is possible to create both an electrically conductive and transparent electrode from a material having a low absorption effect, which is particularly suitable for use in a CT system. The transparency of the electrode refers to the additional irradiation used of the semiconductor, by way of example IR, UV or visible radiation. By using such an electrode firstly the additional radiation passes almost completely to the semiconductor used for detection and secondly, the dose of X-ray radiation used can be kept low as the absorption effect of the electrode is low.

To achieve these effects, i.e. transparency and a low absorption effect, the electrode may be composed of a plurality of layers. The electrically conductive and transparent electrode is attached to a side face of the semiconductor facing the X-ray radiation. A first layer, attached directly to the material of the semiconductor, may be designed as an electrically conductive and at least partially transparent contact layer. Conductive metals such as platinum, indium, molybdenum, tungsten, ruthenium, rhodium, gold, silver, aluminum or a compound of these metals are suitable for this. The contact layer may be designed either as a continuous layer having a thickness of at most 200 nm, or as a porous layer having non-uniformly distributed, transparent pores, or as a structured layer, by way of example in the form of a net having uniformly distributed transparent holes or meshes. At least 10%, preferably at least 50%, of the additional radiation passes through the layer, or the pores, holes or meshes to the material of the semiconductor. By way of example, more radiation passes through the contact layer the thinner it is, and/or the larger or more frequently the pores, holes or meshes are formed. By contrast, however, the conductivity of the contact layer decreases as the number of pores, holes or meshes in the layer increases.

The inventors are, in at least one embodiment, accordingly proposing to further improve a direct-converting X-ray radiation detector for detecting X-ray radiation, in particular for use in a CT system. In at least one embodiment, the direct-converting X-ray radiation detector at least includes a semiconductor used to detect X-ray radiation, and at least one electrode attached to the semiconductor, wherein the semiconductor and the at least one electrode are electrically conductively connected and the at least one electrode is designed to be transparent and electrically conductive such that the at least one electrode attached to the semiconductor at least has the following layers in the following order: at least one contact layer, at least one intermediate layer with at least one filling element embedded in the adhesive agent, at least one TCO layer and at least one support protection layer. The layers of the electrode are preferably located on the semiconductor, starting from the semiconductor in the direction of the incident radiation, in the order mentioned above.

The framework of at least one embodiment of the invention also includes a CT system, at least comprising a direct-converting X-ray radiation detector with which tomographic images of an examination object can be created. In a CT system having the inventive X-ray radiation detector a drift-free measurement of the radiation absorption is advantageously ensured, so the created images are advantageously free from artifacts.

To achieve these effects, i.e. transparency and a low absorption effect, the electrode may be composed of a plurality of layers. The electrically conductive and transparent electrode is attached to a side face of the semiconductor facing the X-ray radiation. A first layer, attached directly to the material of the semiconductor, may be designed as an electrically conductive and at least partially transparent contact layer. Conductive metals such as platinum, indium, molybdenum, tungsten, ruthenium, rhodium, gold, silver, aluminum or a compound of these metals are suitable for this. The contact layer may be designed either as a continuous layer having a thickness of at most 200 nm, or as a porous layer having non-uniformly distributed, transparent pores, or as a structured layer, by way of example in the form of a net having uniformly distributed transparent holes or meshes. At least 10%, preferably at least 50%, of the additional radiation passes through the layer, or the pores, holes or meshes to the material of the semiconductor. By way of example, more radiation passes through the contact layer the thinner it is, and/or the larger or more frequently the pores, holes or meshes are formed. By contrast, however, the conductivity of the contact layer decreases as the number of pores, holes or meshes in the layer increases.

A further electrically conductive and transparent layer may be formed on the contact layer. This layer is designed by way of example as an intermediate layer having a thickness between 25 μm and 300 μm. The intermediate layer comprises an adhesive agent and a plurality of filling elements which are embedded or incorporated in the adhesive agent. The adhesive agent is formed by way of example as an electrically conductive, transparent transfer tape. Adhesive materials, which are at least semi-transparent to the additional radiation, such as acrylates, silicones or other organic adhesives, are suitable for the adhesive agent. The particle-like filling elements are embedded in the adhesive agent and provide an electrically conductive contact between the contact layer and a further layer of the electrode. The filling elements are made, by way of example from a conductive metal such as copper, aluminum, silver, carbon, nickel, gold, or a combination of these materials for this. The number of filling elements or the density thereof in the adhesive agent, as well as the distance between the filling elements, is selected so firstly the intermediate layer is designed to be as conductive as possible but secondly, the intermediate layer is as transparent as possible. In this connection the more filling elements or the greater their density, the higher the conductivity is, but the lower the transparency of the intermediate layer and vice versa. The density can be selected so not more than 75% of the original intensity of the additional radiation is absorbed by the intermediate layer.

The further layer of the electrode is designed by way of example as a TCO layer and by means of the filling elements of the intermediate layer is electrically conductively connected to the contact layer, and therefore to the semiconductor. The abbreviation TCO stands for the English term "transparent conducting oxides". These are electrically conductive materials with a comparatively low absorption of electromagnetic waves in the visible light range. Suitable materials include by way of example inorganic materials such as pure or doped indium tin oxide, pure or doped indium oxide, tin oxide, pure or doped zinc oxide, cadmium oxide, or organic materials such as poly-3,4-ethylene dioxythiophene, polystyrene sulfonate, carbon nanotubes, pure or doped derivatives of polyaniline. The TCO layer has by way of example a thickness of 5 nm to 5 μm.

A further layer in the form of an electrically conductive and transparent support protection layer may also be formed on the TCO layer, made by way of example from polyethylene terephthalate, polyethylene terephthalate glycols, polypropylene, polyethylene, polyvinyl chloride or other plastic-based materials.

The TCO layer and the support protection layer of the electrode may also form an electrically conductive connection of the electrode to a voltage source of the X-ray radiation detector. This connection is formed either as a direct or indirect connection. With a direct connection, the electrode is directly connected to the voltage source, by way of example soldered. With an indirect connection, conductive connecting elements by way of example are formed between the TCO layer and the voltage source.

In at least one embodiment, an electrode comprises a plurality of electrically conductive and transparent layers: measuring processes of the detector can be carried out while the additional radiation is being applied to the semiconductor. The entire surface of the semiconductor can be used for detection of gamma and/or X-ray radiation, in contrast to conventional detectors in which at least part of the surface is covered with a non-transparent electrode and cannot be exposed to additional radiation therefore. Due to the lack of irradiation this region of the semiconductor exhibits unstable behavior time-wise. The absorption effect of the electrode that occurs for the gamma and/or X-ray radiation is much lower compared to the prior art. This is mainly achieved by way of the small thickness of the electrode and the low atomic numbers dependent on the materials selected.

The inventors are, in at least one embodiment, accordingly proposing to further improve a direct-converting X-ray radiation detector for detecting X-ray radiation, in particular for use in a CT system. In at least one embodiment, the direct-converting X-ray radiation detector at least includes a semiconductor used to detect X-ray radiation, and at least one electrode attached to the semiconductor, wherein the semiconductor and the at least one electrode are electrically conductively connected and the at least one electrode is designed to be transparent and electrically conductive such that the at least one electrode attached to the semiconductor at least has the following layers in the following order: at least one contact layer, at least one intermediate layer with at least one filling element embedded in the adhesive agent, at least one TCO layer and at least one support protection layer. The layers of the electrode are preferably located on the semiconductor, starting from the semiconductor in the direction of the incident radiation, in the order mentioned above.

The direct-converting X-ray radiation detector comprises a semiconductor which is used to detect the X-ray radiation. CdTe, CdZnTe, CdZnTeSe, CdTeSe, CdMnTe, InP, TlBr2 or HgI2 by way of example are suitable as the material of the semiconductor. In addition, the X-ray radiation detector comprises at least one electrode attached to the semiconductor. In one embodiment exactly one electrode is formed. Other embodiments provide more than one electrode, by way of example, two, three or four electrodes. The electrode is formed by way of example as an anode and/or a cathode. The inventive electrode is preferably attached to a surface of the semiconductor aligned with the X-ray radiation and/or with the additional radiation. The cathode is also preferably arranged on the side facing the X-ray radiation or the additional radiation since conventional detectors use the electrons for signal generation. The electrode advantageously extends almost over the entire surface of the semi-conductor facing the X-ray radiation. The semiconductor is electrically conductively connected to the electrode. The electrode is also connected to at least one voltage source, in particular a high voltage source. A voltage is applied to the semiconductor by way of the voltage source, so the additionally generated charge carriers move inside the semiconductor toward the electrode in the resulting electric field.

According to at least one embodiment of the invention, the electrode is designed to be both transparent and electrically conductive. This ensures firstly that the additional radiation can penetrate into the semiconductor since there is no shielding of the additional radiation by the transparent electrode and secondly, that an electrically conductive connection to the voltage source is formed. The electrode is in one piece in one embodiment. In other preferred embodiments the electrode has multiple parts, for example two, three, four or five parts. The electrode is constructed by way of example from a plurality of layers. The layers of the electrode advantageously extend respectively parallel to the surface of the semiconductor to which the electrode is attached. One embodiment provides that all layers are transparent and electrically conductive in each case. In another embodiment the layers are transparent and electrically conductive in their entirety.

In one embodiment, the electrode comprises at least one electrically conductive contact layer. Preferably exactly one contact layer is formed; a plurality of contact layers is formed in other embodiments. The contact layer is advantageously attached directly to the semiconductor. It is used for electrically conductive contacting of the electrode with the semiconductor. The contact layer preferably has a thickness of at most 250 nm, preferably at most 200 nm, and more preferably at most 150 nm. Basically the following applies in this case: the thinner the contact layer is, the more transparent it is for the additional radiation, with the conductivity being reduced as the thickness decreases. Electrically conductive metals such as platinum, indium, molybdenum, tungsten, ruthenium, rhodium, gold, silver, aluminum and/or compounds thereof are primarily suitable for the contact layer.

Various embodiments of the contact layer are possible. One embodiment provides a continuous contact layer with the thickness mentioned above. Here the transparency and conductivity of the contact layer are advantageously equal over its entire surface. Other embodiments provide that the contact layer is structured. By way of example, the contact layer is porous. The pores of the contact layer are advantageously more transparent to the additional electromagnetic radiation than the other regions of the contact layer. As the number and/or size of the pores increases, the transparency of the contact layer increases, with the conductivity being reduced at the same time. The contact layer may likewise be structured, by way of example in the manner of a net. A net-like contact layer advantageously has a large number of open meshes or holes which increase the transparency of the contact layer. In contrast to a porous contact layer having non-uniformly distributed pores, the meshes of a net-like contact layer can advantageously be uniformly distributed, so the properties of the contact layer are uniform over the entire surface of the semiconductor. Furthermore, it is possible to design a porous or structured contact layer to be thinner than a continuous contact layer, since, with decreasing thickness of material, the layer spontaneously forms holes or the like as in a thicker layer.

A further layer of the electrode is preferably designed as at least one intermediate layer. Preferably exactly one intermediate layer is formed; a plurality of intermediate layers is formed in other embodiments. The intermediate layer is preferably arranged on the contact layer. The intermediate layer advantageously comprises an adhesive agent and at least one filling element. The adhesive is formed by way of example as an adhesive or self-adhesive material, such as acrylates or other adhesives. The adhesive agent is designed to be at least semi-transparent, preferably transparent, to the additional radiation. The at least one filling element is preferably embedded in the adhesive agent or incorporated therein and therefore surrounded by the adhesive agent.

In one embodiment exactly one filling element is provided. Preferred embodiments provide a plurality of, in particular a large number of, filling elements. The filling elements advantageously implement a conductive connection between the contact layer and a further layer of the electrode. The filling elements are accordingly constructed so as to be electrically conductive, by way of example from a metal such as copper, aluminum, silver, carbon, nickel, gold or combinations thereof. The particle-like filling elements are in the form of silver-plated copper and/or nickel particles or the like by way of example. In one embodiment the particle-like filling elements are designed so as to be elongated, in particular fiber-like and/or cylindrical. Other embodiments provide round filling elements. The filling elements can also be embedded in the adhesive agent so as to be uniformly and/or non-uniformly spaced apart.

The intermediate layer preferably has a thickness of about 25 μm to 300 μm. The thickness is dependent in particular on the shape and size of the filling elements used. The intermediate layer preferably also has an absorption factor of at most 75%, preferably at most 60%, more preferably at most 50% and most preferably at most 40%, of the intensity of the additional radiation. In other words, preferably at most 75% of the additional radiation is blocked by the intermediate layer. The different absorption rates of the intermediate layer are preferably adjustable by means of the number and/or size of the filling elements. The denser and the more filling elements there are present in the adhesive agent, the less transparent the intermediate layer is, but all the more conductive it is. The density is advantageously selected such that the intermediate layer is as transparent as possible but still sufficiently conductive.

The electrode advantageously comprises a further layer with which the intermediate layer, or more precisely the filling elements of the intermediate layer, produce(s) an electrically conductive connection. This further layer is preferably formed as at least one TCO layer. Preferably exactly one TCO layer is formed; a plurality of TCO layers is formed in other embodiments. The abbreviation TCO stands for the term transparent, electrically conductive oxides (English: transparent conducting oxides). The TCO layer is accordingly made from a transparent conductive oxide. TCO materials are electrically conductive materials having a comparatively low absorption of electromagnetic waves in the visible light range. In this respect a TCO layer is particularly suitable for achieving a transparent and electrically conductive electrode.

Organic and inorganic materials are suitable for forming the TCO layer. The TCO layer is advantageously formed from at least one material from the following list: indium tin oxide (ITO, FTO, etc.), pure or doped, indium oxide, pure or doped (In2O3, IZO, etc.), tin oxide (SnOx), zinc oxide (ZTO, AZO, GZO, IZO, etc.), pure or doped, cadmium oxide (CdO), or poly-3,4-ethylene dioxythiophene (PEDOZ), polystyrene sulfonate (PSS), PEDOT:PSS, carbon nanotubes, derivatives of polyaniline, pure or doped. The TCO layer preferably has a thickness of 5 nm to 5 μm.

In a preferred embodiment the electrode includes yet a further layer which is formed as at least one support protection layer. The at least one support protection layer is preferably attached directly to the TCO layer. The at least one support protection layer is also preferably formed as the outermost layer of the electrode which is directly exposed to the X-ray radiation to be detected and to the additional radiation. Preferably exactly one support protection layer is formed; a plurality of support protection layers is formed in other embodiments. The support protection layer is preferably designed to be transparent and electrically conductive. Materials such as polyethylene terephthalate (PET), polyethylene terephthalate glycols (PET-G), polypropylene (PP), polyethylene (PE), polyvinyl chloride (PVC) or the like are suitable for this.

The layers of the electrode are electrically conductively connected together and also provide an electrically conductive connection between the voltage source and the material of the semiconductor. In addition, the layers are transparent in their entirety according to the invention. The layers advantageously extend over an entire side face of the semiconductor or each layer arranged below in each case. A total thickness of the layers or of the electrode is preferably between 50 μm and 510 μm.

The electrode is electrically connected to the at least one voltage source. This electrical connection is either direct or indirect. A direct connection advantageously provides that the electrical connection is formed by the electrode itself. The electrically conductive connection is preferably formed here as a continuation or extension of the at least one TCO layer and the at least one support protection layer. The thicker, more stable TCO layer supports the thinner, less stable support protection layer. The TCO layer of the electrode is accordingly preferably connected directly to the voltage source, by way of example the electrical connection has between a soldered joint, a bonded joint consisting of a conductive adhesive and/or a conductive adhesive tape, and/or a mechanical connection, in particular a clamp connection.

In another embodiment the electrical connection between the electrode and the voltage source is designed as an indirect connection. Here the TCO layer is indirectly connected to the voltage source. The electrical connection advantageously comprises at least one electrically conductive connecting element which electrically conductively connects the TCO layer to the voltage source. An electrical resistance of the electrical connection to the voltage source may be slightly reduced by using connecting elements. One embodiment provides exactly one connecting element; preferred embodiments provide more than one, by way of example two, three or four, connecting elements. The connecting elements are either the same or different.

In an embodiment having two connecting elements, a first connecting element is advantageously connected firstly to the TCO layer and secondly to a second connecting element, with the second connecting element advantageously being connected in turn to the voltage source. In one embodiment the first connecting element is formed from an adhesive agent corresponding to the adhesive agent of the intermediate layer or from some other electrically conductive material, by way of example an adhesive and/or adhesive tape. In one embodiment the second connecting element is made from an electrically conductive metal, in particular a metal film.

In one embodiment the electrical connection of the electrode to the voltage source is formed over an entire width of the electrode or the semiconductor. In another embodiment the electrical connection is narrower than the side of the electrode directed toward the voltage source.

The framework of at least one embodiment of the invention also includes a CT system, at least comprising a direct-converting X-ray radiation detector with which tomographic images of an examination object can be created. In a CT system having the inventive X-ray radiation detector a drift-free measurement of the radiation absorption is advantageously ensured, so the created images are advantageously free from artifacts.

BRIEF DESCRIPTION OF THE DRAWINGS

The invention will be described in more detail below with reference to a preferred example embodiment with the aid of the figures, with only the features necessary for an understanding of the invention being shown. The following reference characters are used: 1: semiconductor, 1a: surface of the semiconductor; 2: electrode; 3: contact layer; 4: intermediate layer; 4a: adhesive agent; 4b: filling element; 5: TCO layer; 6: support protection layer; 7: voltage source; 8: electrically conductive connection; 9: first connecting element; 10: second connecting element; 11: bonded joint, 12: soldered joint; 13: clamp connection, C1: CT system; C2: first X-ray tube; C3: first detector C4: second X-ray tube (optional); C5: second detector (optional); C6: gantry housing; C7: patient; C8: examination table; C9: system axis; C10: arithmetic and control unit; Prg1 to Prgn: computer programs.

In the drawings.

DETAILED DESCRIPTION OF THE EXAMPLE EMBODIMENTS

Figure 1:
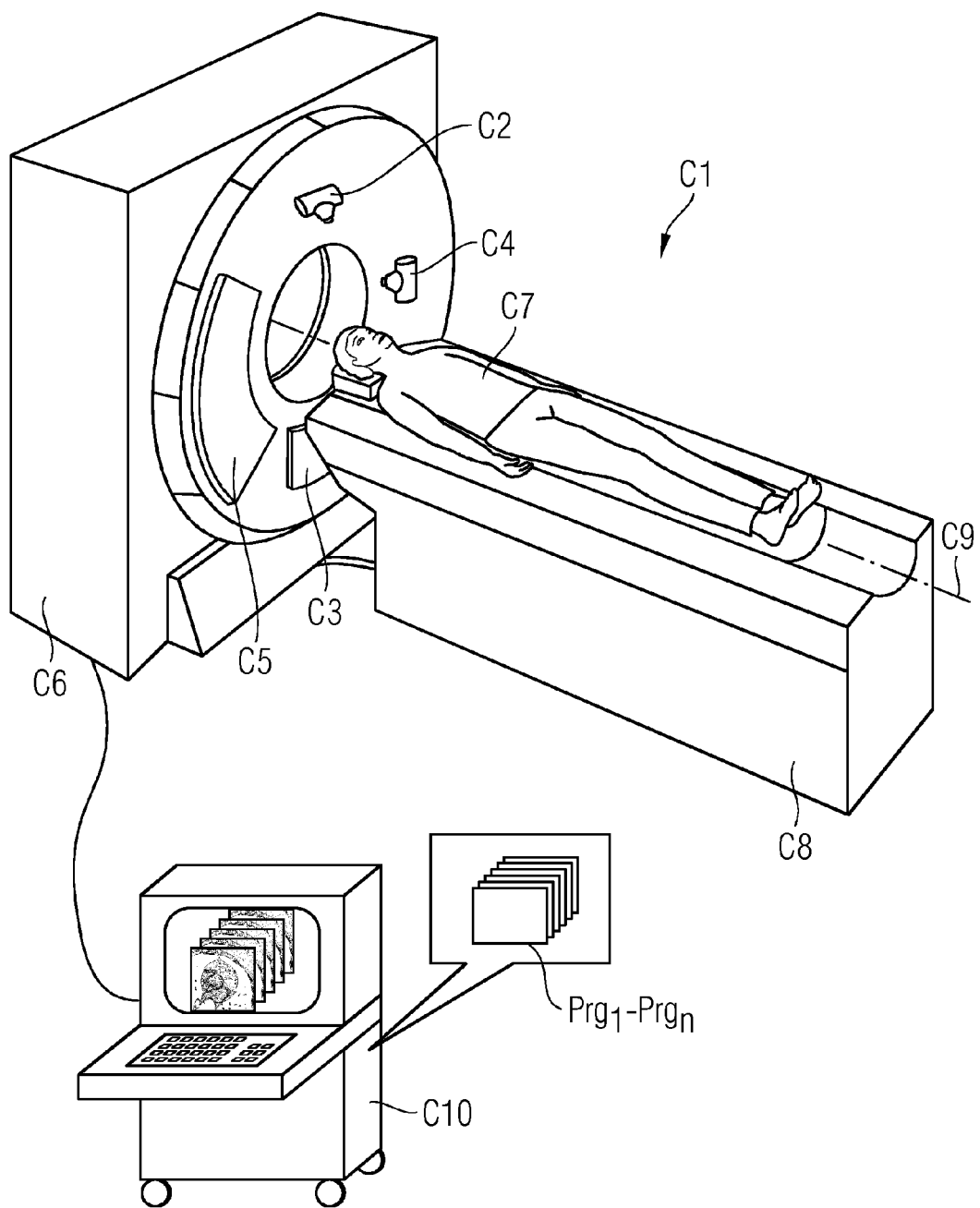
FIG. 1 shows a schematic diagram of a CT system having an arithmetic unit.

FIG. 1 shows an example CT system C1. The CT system C1 includes a gantry housing C6 in which a gantry (not shown here) is located, to which a first X-ray tube C2 having an opposing first detector C3 is secured. A second X-ray tube C4 is optionally provided having a second opposing detector C5. A patient C7 is on an examination table C8 that can be moved in the direction of system axis C9, with which table he can be pushed during the scan with the X-ray radiation continuously or sequentially along the system axis C9 through a measuring field between the X-ray tubes C2 and C4 and the respective associated detectors C3 and C5. This process is controlled by an arithmetic and control unit C10 with the aid of computer programs Prg1 to Prgn.

According to an embodiment of the invention, the detectors C3 and C5 are formed as direct-converting X-ray radiation detectors which have at least one semiconductor used for the detection of the X-ray radiation, and an electrode 2 attached to the semiconductor 1, with the semiconductor 1 and the electrode 1 being electrically conductively connected to a voltage source 7. According to the invention the electrode is designed to be electrically conductive and transparent (see FIGS. 3 to 6).

Figure 2:
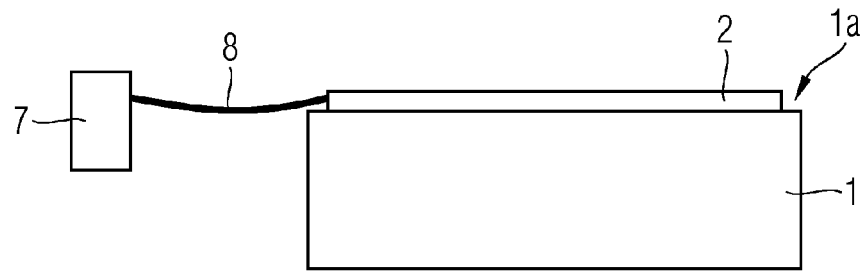
FIG. 2 shows a schematic diagram of a conventional electrode on a semiconductor having a voltage source.

FIG. 2 shows a schematic diagram of a conventional electrode 2 on a semiconductor 2 having a voltage source 7. The semiconductor 1, for example CdTe, is used for the detection of X-ray radiation in a CT system (see FIG. 1), with the semiconductor 1 being irradiated with an additional radiation, by way of example IR radiation, to produce additional charge carriers. The electrode 2 is attached to a surface 1a of the semiconductor 1 directed toward the additional radiation. The electrode 2 and the semiconductor 1 are electrically conductively connected to each other. The electrode 2 is also connected by means of an electrically conductive connection 8 to the voltage source 7 of the detector. According to the conventional embodiment of the electrode 2 shown here this is non-transparent to the additional radiation, so the semiconductor 1 is almost completely shielded from the additional radiation by the electrode 2. The generation of additional charge carriers in the material of the semiconductor 1 is therefore limited.

Figure 3:
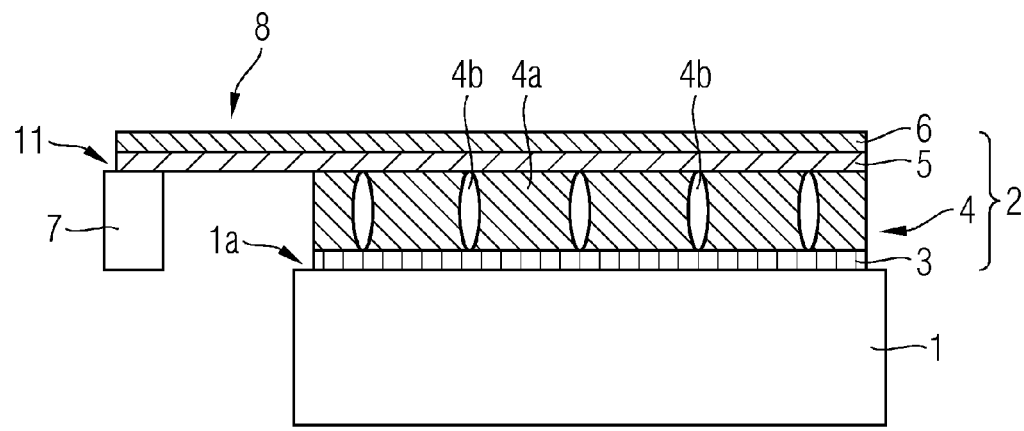
FIG. 3 shows a schematic diagram of an inventive electrode on a semiconductor having a voltage source in a first embodiment.

FIG. 3 shows an inventive electrode 2 on a semiconductor 1 having a voltage source 7. The semiconductor 1, voltage source 7 and arrangement of the electrode 2 on the semiconductor 1 match the embodiment shown in FIG. 2. The same components are denoted by the same reference characters. A detailed description of components already described will be omitted therefore.

According to an embodiment of the invention, the electrode 2 is designed to be transparent and electrically conductive. The electrode 2 comprises four respectively transparent and electrically conductive layers, namely a contact layer 3, an intermediate layer 4, a TCO layer 5 and a support protection layer 6. The individual layers 3, 4, 5 and are moreover also electrically conductively connected to each other in each case. The layers are attached in the above order to the surface 1a of the semiconductor 1, with the contact layer 3 being contacted directly by the surface 1a, and the support protection layer 6 being directly exposed to the incident radiation. A thickness of the electrode 2 and a total thickness of the layers 3, 4, 5 and 6 is between 50 μm and 510 μm.

The contact layer 3 is made from an electrically conductive metal, such as platinum. In the embodiment shown here the contact layer 3 is also designed as a continuous layer having a uniform thickness of less than 200 nm. Due to the small thickness of the contact layer 3 it is at least partially transparent to the additional radiation.

The intermediate layer 4 is attached to the contact layer 3. The intermediate layer 4 comprises an adhesive and at least partially transparent adhesive agent 4a such as an electrically conductive adhesive. The intermediate layer 4 also comprises a plurality of electrically conductive, particle-like filling elements 4b. The filling elements 4b are embedded in the adhesive agent 4 and provide an electrically conductive connection between the contact layer 3 and TCO layer 5 arranged on the intermediate layer 4. In the embodiment shown here the filling elements 4b are evenly spaced apart and formed as elongated fibers. The filling elements 4b are formed, by way of example, from a metal.

The TCO layer 5 is also attached to the intermediate layer 4. The electrically conductive and transparent TCO layer 5 is made from electrically conductive materials having a low absorption factor for the additional radiation, for example doped indium oxide. The support protection layer 6 is attached to the TCO layer as the outermost or uppermost layer. The transparent support protection layer 6 has a thickness of about 100 μm and is made by way of example from PET.

These two layers, i.e. the TCO layer 5 and the support protection layer 6, form a direct, electrically conductive connection 8 to the voltage source 7. For this the TCO layer 5 and the support protection layer 6 are extended or continued up to the voltage source 7. The thinner, upper support protection layer 6 is supported and stabilized by the thicker TCO layer 5. The embodiments of FIGS. 3 to 5 differ in the configuration of the direct connection of the TCO layer 5 to the voltage source 7. According to FIG. 3 the electrically conductive connection 8 has a bonded joint 11 by means of which the TCO layer is glued to the voltage source 7.

Figure 4:
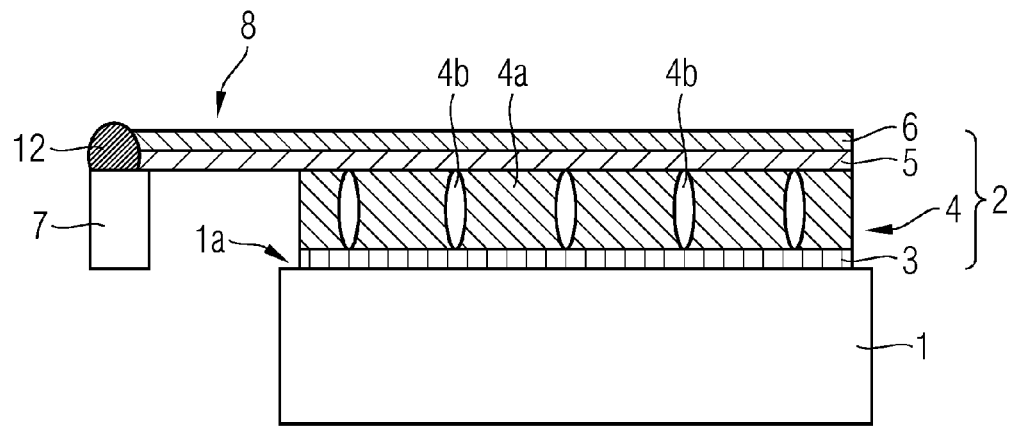
FIG. 4 shows a schematic diagram of the inventive electrode on a semiconductor having a voltage source and a direct connection to the voltage source in a first embodiment.
Figure 5:
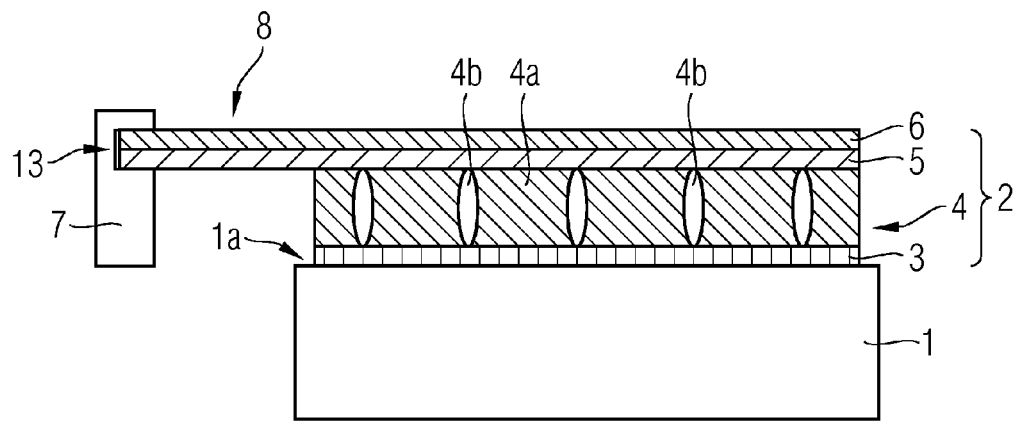
FIG. 5 shows a schematic diagram of the inventive electrode according to FIG. 4, and the direct connection in a further embodiment.

In the embodiment of FIG. 4 the electrically conductive connection 8 comprises a soldered joint 12 for connecting the TCO layer 5 to the voltage source 7. In the embodiment of FIG. 5 the TCO layer 5 is electrically conductively connected to the voltage source by means of a clamp connection 13. The embodiments of the semiconductor 1, the electrode 2 with its layers 3, 4, 5 and 6 of FIGS. 4 and 5 match the embodiment shown in FIG. 2, moreover. Identical components are designated by identical reference characters. A detailed description of components already described will be omitted therefore.

Figure 6:
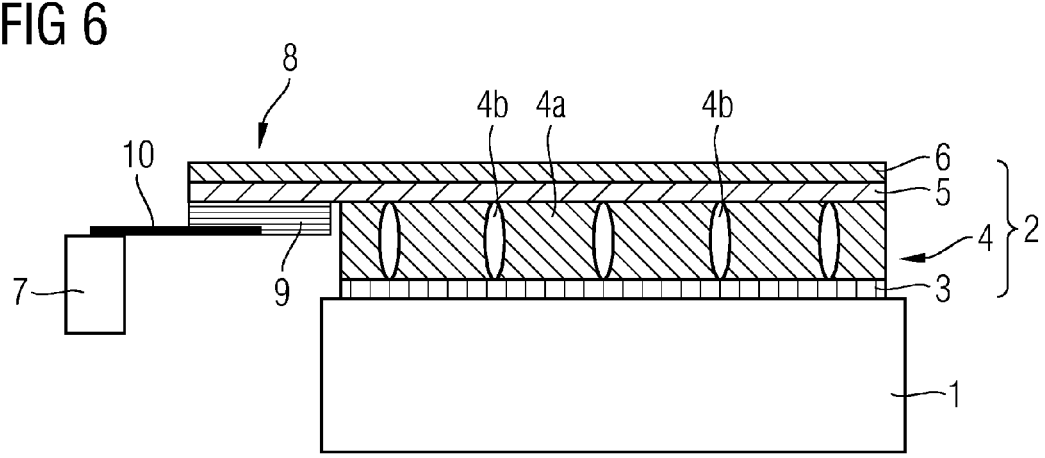
FIG. 6 shows a schematic diagram of an embodiment of the inventive electrode of FIG. 3 having an indirect connection to the voltage source.

FIG. 6 shows a schematic diagram of an embodiment of the inventive electrode 2 having an indirect, electrically conductive connection 8 to the voltage source 7. The embodiment of the electrode 2 of FIG. 6 matches the embodiment of FIG. 3. Identical components are designated by identical reference characters. A detailed description of components already described will be omitted therefore. The embodiment of FIG. 6 differs only in the design of the electrically conductive connection 8 of the electrode 2 to the voltage source 7, namely in the form of an indirect connection 8. Here the connection 8 includes two electrically conductive connecting elements 9 and 10, which connect the electrode 2, more precisely the TCO layer 5, to the voltage source 7. The TCO layer 5 and the support protection layer 6 are also formed as continuations or extensions beyond the surface of the semiconductor 1 in this embodiment. The first connecting element 9 is connected firstly to the TCO layer 5 and secondly to the second connecting element 10. The second connecting element 10 is still connected to the voltage source 7, by way of example soldered. In the embodiment shown here the first connecting element 9 is designed as an electrically conductive adhesive tape, and the second connecting element 10 as a conductive metal film.

Figure 7:
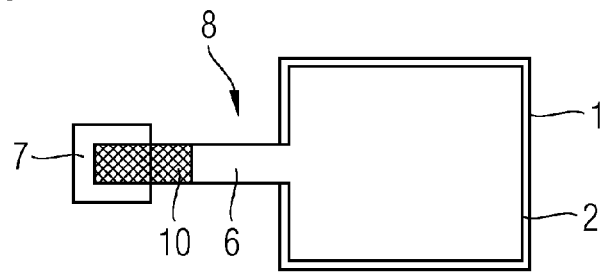
FIG. 7 shows a schematic plan view of an embodiment of the inventive electrode in FIG. 6 having the indirect connection.

FIG. 7 shows a schematic plan view of an embodiment of the inventive electrode 2 according to FIG. 6 having the indirect connection 8 to the voltage source 7. The electrode 2 and its arrangement on the semiconductor 1 match the embodiment of FIG. 6. The plan view of FIG. 7 shows that the electrical connection 8 is narrower than the side of the semiconductor 1 directed toward the voltage source 7. The support protection layer 6 and TCO layer (not visible in the plan view) are formed as a continuation and are electrically conductively connected to the voltage source 7 by means of the two connecting elements. Here only the second connecting element 10, which connects the first connecting element and the electrode 2 to the voltage source 7, is shown.

Although the invention has been illustrated and described in detail by way of the preferred example embodiment, it is not limited by the disclosed examples and a person skilled in the art can derive other variations herefrom without departing from the scope of the invention.

The invention claimed is:

1. A direct-converting X-ray radiation detector for detecting X-ray radiation, comprising:
   a semiconductor, to detect X-ray radiation; and
   at least one electrode attached to the semiconductor, wherein the semiconductor and the at least one electrode are electrically conductively connected and the at least one electrode is designed to be transparent and electrically conductive, the at least one electrode including at least:
   at least one contact layer attached to the semi-conductor,
   at least one intermediate layer with at least one filling element embedded in an adhesive agent,
   at least one TCO layer, and
   at least one support protection layer, wherein at least one electrical connection is formed between the at least one electrode and at least one voltage source and wherein the at least one electrical connection includes a continuation of the at least one TCO layer.

2. The X-ray radiation detector of claim 1, wherein the at least one contact layer is designed to be at least partially transparent.

3. The X-ray radiation detector of claim 1, wherein the at least one contact layer includes a thickness of at most 250 nm.

4. The X-ray radiation detector of claim 1, wherein the at least one contact layer is porous, and wherein the pores of the at least one contact layer are transparent to electromagnetic radiation.

5. The X-ray radiation detector of claim 1, wherein the at least one contact layer is designed like a net.

6. The X-ray radiation detector of claim 1, wherein the at least one contact layer is formed from at least one material from the following list: platinum, indium, molybdenum, tungsten, ruthenium, rhodium, gold, silver, and aluminum.

7. The X-ray radiation detector of claim 1, wherein the adhesive agent is designed to be at least semi-transparent, for electromagnetic radiation.

8. The X-ray radiation detector of claim 1, wherein the at least one filling element forms a conductive connection between the at least one contact layer and a further layer of the at least one electrode.

9. The X-ray radiation detector of claim 1, wherein the at least one filling element is formed from a metal.

10. The X-ray radiation detector of claim 1, wherein the at least one intermediate layer includes an absorption factor of at most 75% of the intensity of the additional radiation.

11. The X-ray radiation detector of claim 1, wherein the at least one TCO layer is formed from at least one material from the following list: indium tin oxide, pure or doped, indium oxide, pure or doped, tin oxide, zinc oxide, pure or doped, cadmium oxide or poly-3,4-ethylene dioxythiophene, polystyrene sulfonate, carbon nanotubes, derivatives of polyaniline, pure or doped.

12. The X-ray radiation detector of claim 1, wherein the at least one support protection layer is formed from at least one material from the following list: polyethylene terephthalate, polyethylene terephthalate glycols, polypropylene, polyethylene, and polyvinyl chloride.

13. The X-ray radiation detector of claim 1, wherein at least one electrical connection is formed between the at least one electrode and at least one voltage source.

14. The X-ray radiation detector of claim 13, wherein the at least one electrical connection between the at least one TCO layer and the at least one voltage source is a mechanical connection.

15. The X-ray radiation detector of claim 13, wherein the at least one electrical connection comprises at least one electrically conductive connecting element.

16. The X-ray radiation detector of claim 15, wherein a first connecting element is connected firstly to the at least one TCO layer and secondly to a second connecting element.

17. The X-ray radiation detector of claim 16, wherein the second connecting element is connected to the at least one voltage source.

18. The X-ray radiation detector of claim 16, wherein the second connecting element is formed from a conductive metal.

19. X-ray radiation detector of claim 1, wherein the at least one electrical connection is formed as a continuation of the at least one TCO layer and the at least one support protection layer.

20. A direct-converting X-ray radiation detector for detecting X-ray radiation, comprising:
   a semiconductor, to detect X-ray radiation; and
   at least one electrode attached to the semiconductor, wherein the semiconductor and the at least one electrode are electrically conductively connected and the at least one electrode is designed to be transparent and electrically conductive, the at least one electrode including at least
   at least one contact layer attached to the semi-conductor,
   at least one intermediate layer with at least one filling element embedded in an adhesive agent,
   at least one TCO layer, and
   at least one support protection layer, wherein at least one electrical connection is formed between the at least one electrode and at least one voltage source and wherein the at least one electrical connection between the at least one TCO layer and the at least one voltage source includes a soldered joint.

21. A direct-converting X-ray radiation detector for detecting X-ray radiation, comprising:
   a semiconductor, to detect X-ray radiation; and
   at least one electrode attached to the semiconductor, wherein the semiconductor and the at least one electrode are electrically conductively connected and the at least one electrode is designed to be transparent and electrically conductive, the at least one electrode including at least
   at least one contact layer attached to the semi-conductor,
   at least one intermediate layer with at least one filling element embedded in an adhesive agent,
   at least one TCO layer, and
   at least one support protection layer, wherein at least one electrical connection is formed between the at least one electrode and at least one voltage source and wherein the at least one electrical connection between the at least one TCO layer and the at least one voltage source includes a bonded joint of at least one of a conductive adhesive and a conductive adhesive tape.

22. A direct-converting X-ray radiation detector for detecting X-ray radiation, comprising:
   a semiconductor, to detect X-ray radiation; and
   at least one electrode attached to the semiconductor, wherein the semiconductor and the at least one electrode are electrically conductively connected and the at least one electrode is designed to be transparent and electrically conductive, the at least one electrode including at least at least one contact layer attached to the semi-conductor, at least one intermediate layer with at least one filling element embedded in an adhesive agent, at least one TCO layer, and at least one support protection layer, wherein the at least one electrical connection comprises at least one electrically conductive connecting element and wherein the first connecting element, as an adhesive agent corresponding to the adhesive agent of the intermediate layer, is formed from at least one of a conductive adhesive and a conductive adhesive tape.

23. A CT system, comprising:

a direct-converting X-ray radiation detector for detecting X-ray radiation, including a semiconductor, to detect X-ray radiation; and at least one electrode attached to the semiconductor, wherein the semiconductor and the at least one electrode are electrically conductively connected and the at least one electrode is designed to be transparent and electrically conductive, the at least one electrode including at least at least one contact layer attached to the semi-conductor, at least one intermediate layer with at least one filling element embedded in an adhesive agent, at least one TCO layer, and at least one support protection layer.

24. The CT system of claim 23, wherein the at least one contact layer is designed to be at least partially transparent.

25. The CT system of claim 23, wherein the at least one contact layer includes a thickness of at most 200 nm.

26. The CT system of claim 23, wherein the at least one contact layer includes a thickness of at most 150 nm.

27. The CT system of claim 23, wherein the adhesive agent is designed to be transparent, for electromagnetic radiation.

28. The CT system of claim 23, wherein the at least one electrical connection between the at least one TCO layer and the at least one voltage source includes a soldered joint.

29. The CT system of claim 23, wherein at least one electrical connection is formed between the at least one electrode and at least one voltage source and wherein the at least one electrical connection includes a continuation of the at least one TCO layer.

30. The CT system of claim 29, wherein the at least one electrical connection is formed as a continuation of the at least one TCO layer and the at least one support protection layer.

* * * * *